United States Patent

Bruttig

[11] 4,120,658
[45] Oct. 17, 1978

[54] METHOD AND APPARATUS FOR DETERMINATION OF DISSOCIATION OF OXYGEN FROM BLOOD

[76] Inventor: Stephen P. Bruttig, 9424 Grand Ave., Omaha, Nebr. 68134

[21] Appl. No.: 741,100

[22] Filed: Nov. 11, 1976

[51] Int. Cl.² .................... G01N 27/00; G01N 33/16
[52] U.S. Cl. ............................. 23/230 B; 324/30 R; 422/68; 422/69
[58] Field of Search .............. 23/230 B, 253 R, 259; 73/19; 324/29, 30 R, 71 R (U.S. only)

[56] References Cited

U.S. PATENT DOCUMENTS

| 3,639,829 | 2/1972 | Harmoncourt | 23/230 B X |
| 3,681,255 | 8/1972 | Wilfore | 23/230 B X |
| 3,874,850 | 4/1975 | Sorensen et al. | 23/230 B |
| 4,013,417 | 3/1977 | Raffaele | 23/230 B X |
| 4,014,649 | 3/1977 | Kiesow | 23/230 B |

OTHER PUBLICATIONS

M. A. Duvelleroy et al., "An Oxyhemoglobin Dissociation Analyzer", Jour. of Applied Physiology, vol. 28, No. 2, pp. 227-233 (Feb. 1970).

J. D. Torrance et al., "Methods for Determination of O₂ Dissociation Curves, Including Bohr Effect", Respiratory Physiology, vol. 8, pp. 127-136, (1969/1970).

Primary Examiner—Joseph Scovronek
Attorney, Agent, or Firm—Henderson, Strom, Sturm, Cepican & Fix

[57] ABSTRACT

Method and apparatus are disclosed for the determination of the dissociation characteristics of oxygen from blood. The functional relationship between increasing liquid phase $P_{O_2}$ and decreasing pH is determined and presented in the form of a continuous curve for values ranging from desaturation to saturation. By analyzing this data through linear regression techniques, the characteristic parameter of the oxygen dissociation curve $P_{50}$, may be easily determined.

6 Claims, 2 Drawing Figures

METHOD AND APPARATUS FOR DETERMINATION OF DISSOCIATION OF OXYGEN FROM BLOOD

BACKGROUND OF THE INVENTION

The dissociation of oxygen from the hemoglobin molecule, an intregal part of the transport of oxygen, can be described by the oxyhemoglobin dissociation curve. This assessment of the respiratory function of the blood takes on clinical significance in the characterization of congenital hemoglobinopathies, in evaluation of blood oxygen transport capability during respiratory and metabolic acid-base disturbances, and more recently in the evaluation of certain forms of ischemic heart disease. The oxyhemoglobin dissociation curve, together with its characteristic parameter $P_{50}$, the partial pressure of oxygen at half-saturation of hemoglobin with oxygen, is known to be affected by changes in temperature, the partial pressure of carbon dioxide, pH, blood organic phosphate concentration and hemoconcentration. Furthermore, the dissociation of oxygen from hemoglobin or whole blood can best be described by a method which measures or controls the majority of these variables, while recording the dissociation process. Presently, there are many methods available for oxygen dissociation curve analysis as, for example, those described by J. D. Torrance and C. Lenfant, in an article entitled "Methods For Determination of $O_2$ Dissociation Curves, Including Bohr Effect", *Respiratory Physiology*, Volume 8, pages 127-136 (1970). The most acceptable of these are methods which record the oxyhemoglobin dissociation reaction as a continuous function of blood oxygen tension, and which continuously record pH change in order to assess the Bohr effect on the hemoglobin-oxygen reaction.

The Laver method, described in an article by M. A. Duvelleroy, R. G. Buckles, S. Rosenkaimer, C. Tung and M. B. Laver, entitled "An Oxyhemoglobin Dissociation Analyzer", published in the *Journal of Applied Physiology*, Volume 28, pages 227-233 (1970), characterizes the oxyhemoglobin dissociation process in this manner. However, this method falls short of perfect assessment of this equilibrium reaction, because it fails to account for changes in the intracellular hydrogen ion concentration or the transcellular hydrogen ion gradient caused by fluctuations in the concentration of the impermeable intracellular anion 2,3-diphosphoglycerate (2,3-DPG). At present there exists no satisfactory prediction formula for the correction of $P_{50}$ due to changes in 2,3-DPG concentration. Nevertheless, 2,3-DPG concentration can be measured separately and the $P_{50}$ can be interpreted in light of its 2,3-DPG magnitude. Finally, the clinical usefulness of even the Laver apparatus is limited, however, by such factors as cost of apparatus, occasional instability of the gas phase $P_{O_2}$ electrode, time of procedure, method for calculation of $P_{50}$, and sample size. The latter of these is a critical limitation in that newborns and young infants do not have a blood volume large enough to justify such a blood sample (approximately 8.0 ml).

SUMMARY OF THE INVENTION

It is an object of this invention to provide an apparatus for the determination of the dissociation characteristics of oxygen from blood which is simple in construction, inexpensive of manufacture and extremely reliable in use.

It is another object of this invention to provide a simple method for determining the dissociation characteristics of oxygen from blood.

It is another object of this invention to provide method and apparatus for the determination of the dissociation characteristics of oxygen from blood which produce the desired results more quickly than heretofore known.

Another object of this invention is to provide method and apparatus for the determination of the dissociation characteristics of oxygen from blood which produce the desired results with smaller blood samples than heretofore required.

It is an even still further object of this invention to provide method and apparatus for the determination of the dissociation characteristics of oxygen from blood which are more reliable than prior art methods and apparatus.

These, and other, objects are obtained according to the instant invention by providing method and apparatus for the determination of the dissociation characteristics of oxygen from blood. The functional relationship between increasing liquid phase $P_{O_2}$ and decreasing pH is determined and presented in the form of a continuous curve for values ranging from desaturation to saturation. By analyzing this data through linear regression techniques, the characteristic parameter of the oxygen dissociation curve, $P_{50}$, may be easily determined.

BRIEF DESCRIPTION OF THE DRAWINGS

For a better understanding of the invention as well as other objects and further features thereof, reference is made to the following detailed disclosure of the invention taken in conjunction with the accompanying drawings wherein.

DESCRIPTION OF THE PREFERRED EMBODIMENTS

The descriptive parameter of the oxyhemoglobin dissociation curve, $P_{50}$, may be defined as the liquid phase oxygen tension, i.e., whole blood or hemoglobin solution, at which the hemoglobin is half saturated with oxygen. The instant invention relies upon the fact that $P_{50}$ may be determined as the mid-point of the pH vs. $P_{O_2}$ (liquid) curve, which is characteristic of the dissociation reaction.

Figure 1:
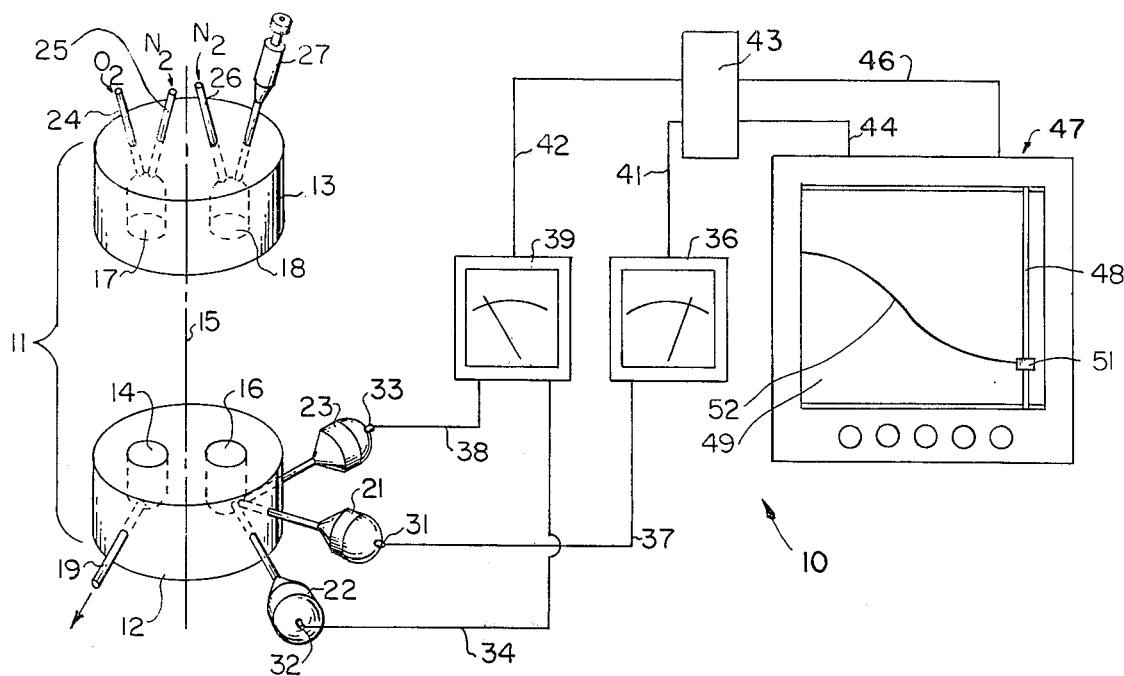
FIG. 1 is a schematic representation of the apparatus of the instant invention.

Referring now to FIG. 1, there is shown the general apparatus arrangement, 10, according to the instant invetion. A reaction block 11 comprises a bottom section 12 and a top section 13, lapped together for a sealing relationship and mounted on a common central axis 15. The two sections 12 and 13 are shown separated in the drawing; however, during use they are in intimate contact with each other as shown by the dotted lines. The top section 13 can be rotated 180° relative to the bottom section 12 for reasons to be explained below.

Each of sections 12 and 13 contain two half chambers 14, 16, 17 and 18 arranged symmetrically about central axis 15, and by making the 180° rotation of section 13 the cooperative relationship between the half chambers may be changed. More specifically, initially the half chambers 14 and 17 make up a complete chamber 14–17 and half chambers 16 and 18 make up a complete chamber 16–18; however, rotation of section 13 makes new complete chambers 14–18 and 16–17.

Half chamber 14 contains an outlet passage 19 through which gases may pass to either a reservoir or the atmosphere. Half chamber 16 is in communication with the ends of three instrument holders 21, 22 and 23, the function of which will be further described below. A source of oxygen gas (97% oxygen—3% $CO_2$), not shown, is in fluid communication with half chamber 17 via tube 24. Half chamber 18 is in communication with a source of nitrogen gas, also not shown, via tube 26. Finally, half chamber 18 is further in communication with sample inlet control device 27.

Instrument holders 21, 22 and 23 are designed to sealingly accept, respectively, a liquid phase $P_{O2}$ electrode 31, a calomel electrode 32 and a pH electrode 33. The $P_{O2}$ electrode measures the partial pressure of oxygen of the liquid sample to be placed within the chamber. Calomel electrode 32 provides a reference measurement relative to the sample pH to insure accurate pH measurement by the electrode 33. Each of the electrodes is in communication with the interior of half chamber 16 so that intimate contact may be made with the sample placed therein.

$P_{O2}$ electrode 31 is electrically connected via line 37 to meter 36 which provides a visual indication of the variation of the partial pressure of oxygen within the sample. Similarly, electrodes 32 and 33 are connected, respectively, via lines 34 and 38 to meter 39 which shows the continuous changes in pH.

The signals generated by meters 36 and 39 are fed, via lines 41 and 42, to an interface unit 43. The interface unit merely modifies the incoming electrical signals to a voltage and pattern suitable for input to X-Y recorder 47. The modified signals are transferred from unit 43 to recorder 47 through lines 44 and 46.

Recorder 47 includes an arm 48 which traverses paper 49 in a left-to-right direction. Simultaneously with the movement of arm 48, slidable pen 51 moves vertically on the arm. The signal from pH meter 39 controls movement of pen 51 in the Y-direction, and the signal from $P_{O2}$ meter 36 controls the X-movement of arm 48. The resulting printed curve 52, as will be described further below, represents the relationship between changing pH and liquid phase partial pressure of oxygen.

In operation, the reaction block 11 is positioned to define complete chambers 14–17 and 16–18. Oxygen is flushed through chamber 14–17 via tube 24 and outlet tube 19 to provide an oxygen atmosphere therein. Chamber 16–18 is then, or simultaneously with the oxygen flush of chamber 14–17, flushed with a nitrogen gas through inlet 26 and out through sample control device 27 to provide a 100% nitrogen atmosphere therein. A blood sample of from about ½ ml to about 4 ml. is then inserted into the chamber 16–18 by inserting a syringe through sample control device 27 and forcing the blood into the chamber. The sample has been "tonometered", to a partial pressure of oxygen equal to zero, i.e., the oxygen has been driven out in a nitrogen flush. The oxygen may be taken from the blood either before insertion into the chamber 16–18 or thereafter by continuing the nitrogen flow through tube 26 and control device 27. The process may be aided by inclusion of a magnetic stirring rod within the half chamber 16 to continuously agitate the sample. Thus, the initial conditions of chamber 14–17 having an oxygen rich atmosphere and the sample having a partial pressure of oxygen equal to zero have been created.

Section 13 of reaction block 11 is then rotated through 180° to reposition half chambers 17 and 18 above, respectively, half chambers 16 and 14. Chamber 16–17 thus contains a sample having a partial pressure of oxygen equal to zero below an oxygen rich atmosphere. Chamber 14–18 is no longer of any consideration and the contents thereof may be flushed to a waste reservoir.

As the oxygen in half chamber 17 is absorbed by the blood sample in half chamber 16 over a period of time, electrodes 31, 32 and 33 measure the changes therein. The changes are read visually on meters 36 and 39 and are printed out on the X-Y recorder 47. As the oxygen is being absorbed by the blood sample pressure variations may occur in half chamber 17, so, to alleviate this a nitrogen bleed 25 is used to admit small amounts of gas from a source, not shown.

Figure 2:
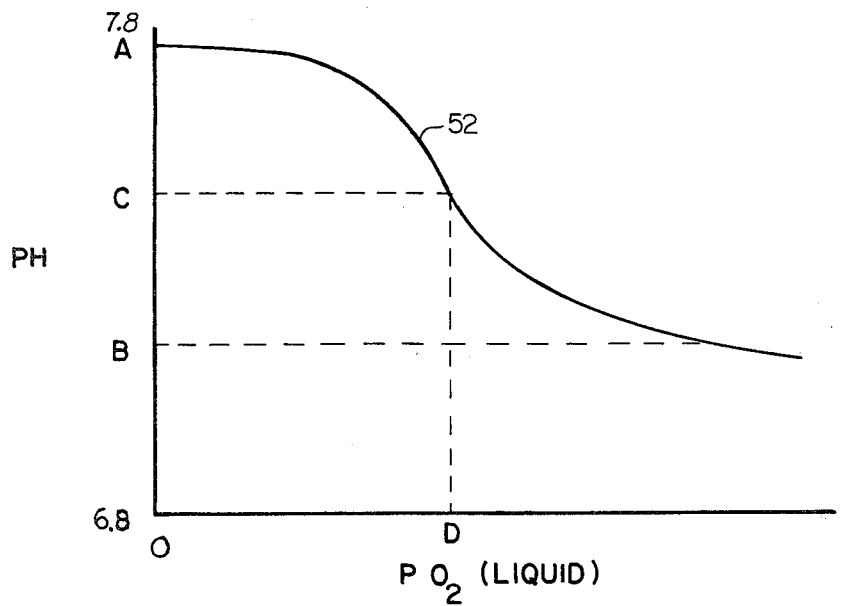
FIG. 2 is a graph showing the curve generated by employment of the method and apparatus of the instant invention.

Referring now to FIG. 2, the curve printed on X-Y recorder 47 can be seen. The changes in partial pressure of oxygen in the liquid sample are in the X-direction and the changes in pH are shown in the Y-direction ranging from 6.8 to 7.8. The curve 52 starts at point A, which represents zero saturation and levels off at point B which represents 100% saturation. Half way between points A and B a line C is extended horizontally to intersect curve 52 to determine $P_{50}$ at point D. Point D thus represents the partial pressure of oxygen at 50% saturation.

One of ordinary skill in the art will readily recognize and understand the various elements which together comprise the novel apparatus and method of the instant invention. All of the structural components mentioned above except the X-Y recorder are available from RADIOMETER of Copenhagen, Denmark, and distributed in the United States by the London Company, 811 Sharon Drive, Cleveland, Ohio. For example, the RADIOMETER parts numbers correspond with the elements as follows:

pH meters — PHM 71
interface — L101
$P_{O2}$ electrode — E5043-0
pH electrode — G267C
calomel electrode — K4018

A suitable reaction block and associated hardware is also sold by RADIOMETER under the designation DCA-1. It should be noted at this time that the reaction block 11 preferably includes other hardware, not shown, such as thermostatic controls and gas humidifiers. These elements are not shown or described in detail because they are well known in the art and contribute only insignificantly to the instant invention.

Any suitable X-Y recorder may be used to graph the output of the instrumentation. Obviously, even an X-Y-Y recorder such as a Honeywell model 540 may be used, without employing the second Y-axis printer.

It will be understood various changes in the details, materials, steps and arrangements of parts, which have herein been described and illustrated in order to explain the nature of the invention, will occur to and may be made by those skilled in the art upon a reading of the disclosure within the principles and scope of the invention.

For example, it is contemplated an important advantage may be attained by making half chambers 14, 16, 17 and 18 quite small and accordingly modifying the location of the insertion points of electrodes 31, 32 and 33. It

I claim:

1. A method for determination of the dissociation of oxygen from blood comprising the steps of:
    (a) providing a sample of blood having a partial pressure of oxygen equal to zero;
    (b) placing an oxygen atmosphere of at least 97% oxygen above, and in contact with, the surface of said sample of blood;
    (c) simultaneously monitoring the changes in the pH and partial pressure of oxygen in the liquid phase and not the gaseous phase in said sample of blood as the oxygen is absorbed, said monitoring including the production of a continuous curve of increasing liquid phase partial pressure of oxygen v. decreasing pH from desaturation to saturation of said sample of blood with oxygen; and
    (d) analyzing said curve to determine the partial pressure of oxygen at 50% saturation by intersecting said curve with a horizontal line beginning at a point ½ the distance between saturation and desaturation and then vertically expanding the point of intersection to determine the partial pressure of oxygen.

2. The method of claim 1 wherein said monitoring step (c) is done electronically by contacting said sample of blood with a liquid phase P02 electrode, a calomel electrode and a pH electrode and using the electrical signals generated thereby to control an X-Y recorder.

3. The method of claim 2 wherein said sample of blood is not larger than 4 ml in volume.

4. Apparatus for determination of the dissociation of oxygen from blood comprising:
    (a) a sample control means including a bottom section and an opposing top section rotatably mounted on a common central axis, each of said top and bottom sections having first and second half chambers therein arranged symmetrically about said central axis such that said first half chambers oppose each other to form a complete chamber and said second half chambers oppose each other to also form a complete chamber;
    (b) an oxygen gas inlet extending through said top section into said first half chamber therein;
    (c) a nitrogen gas inlet extending through said top section into said first half chamber therein;
    (d) a gas outlet extending through said bottom section into said first half chamber therein;
    (e) a nitrogen gas inlet extending through said top section into said second half chamber therein;
    (f) a blood sample inlet extending through said top section into said second half chamber therein;
    (g) a calomel electrode, a pH electrode and a liquid phase $P_{02}$ electrode each extending through said bottom section into said second half chamber therein, no provision being made for a gaseous phase $P_{02}$ electrode; and,
    (h) an X-Y chart recorder electrically connected for movement in the Y-direction to said calomel and pH electrodes, and connected for movement in the X-direction to the liquid phase $P_{02}$ electrode.

5. The apparatus of claim 4 wherein said second half chamber in said bottom section has a volume of less than 4 ml.

6. The apparatus of claim 5 wherein said electrical connections in part (h) include meters for giving a visual indication of signal strength.

UNITED STATES PATENT AND TRADEMARK OFFICE
CERTIFICATE OF CORRECTION

PATENT NO. : 4,120,658
DATED : October 17, 1978
INVENTOR(S) : Stephen P. Bruttig It is certified that error appears in the above–identified patent and that said Letters Patent are hereby corrected as shown below:

Claim 2, line 29, the reference "PO2" should read $--P_{O2}--$

Signed and Sealed this

Sixth Day of February 1979

[SEAL]

Attest:

RUTH C. MASON
*Attesting Officer*

DONALD W. BANNER
*Commissioner of Patents and Trademarks*